US004001698B2

United States Statutory Invention Registration [19]

[11] Reg. Number: H1698

[45] Published: Nov. 4, 1997

Lloyd et al.

[54] ABSORBENT STRUCTURES HAVING THERMALLY BONDED RESILIENT WEB FOR IMPROVED FIT AND COMFORT

[75] Inventors: Susan Nicole Lloyd, Middletown, Ohio; Sheri D. Keeler, W. Harrison, Ind.

[73] Assignee: The Procter & Gamble Company, Cincinnati, Ohio

[21] Appl. No.: 327,082

[22] Filed: Oct. 21, 1994

[51] Int. Cl.[6] ..... A61F 13/46

[52] U.S. Cl. ..... 604/378; 604/358

[58] Field of Search ..... 604/358, 378, 604/370, 367, 385.11

[56] References Cited

U.S. PATENT DOCUMENTS

| | | | |
|---|---|---|---|
| 4,425,126 | 1/1984 | Butterworth et al. | 604/366 |
| 4,500,315 | 2/1985 | Pieniak et al. | 604/379 |
| 4,537,590 | 8/1985 | Pieniak et al. | 604/379 |
| 4,540,454 | 9/1985 | Pieniak et al. | 156/62.2 |
| 4,573,988 | 3/1986 | Pieniak et al. | 604/379 |
| 4,578,068 | 3/1986 | Kramer et al. | 604/368 |
| 4,578,070 | 3/1986 | Holtman | 604/378 |
| 4,596,567 | 6/1986 | Iskra | 604/368 |
| 4,600,458 | 7/1986 | Kramer et al. | 156/199 |
| 4,605,402 | 8/1986 | Iskra | 604/368 |
| 4,640,810 | 2/1987 | Laursen et al. | 264/518 |
| 4,652,484 | 3/1987 | Shiba et al. | 428/286 |

(List continued on next page.)

FOREIGN PATENT DOCUMENTS

| | | |
|---|---|---|
| 0 165 807 | 12/1985 | European Pat. Off. . |
| 0 337 296 | 10/1989 | European Pat. Off. . |

(List continued on next page.)

*Primary Examiner*—Michael J. Carone
*Assistant Examiner*—Matthew J. Lattig
*Attorney, Agent, or Firm*—William Scott Andes; E. Kelly Linman; Jacobus C. Rasser

[57] ABSTRACT

The present invention provides absorbent structures for absorbent articles, in particular catamenial pads, that are capable of acquiring, distributing, and storing aqueous body fluids, especially menstrual fluids, as well as providing better fit and comfort for the user of the products. These absorbent structures comprise an absorbent core and a comparatively low density, fluid-pervious, resilient web in fluid communication with the absorbent core. The resilient webs of the present invention are formed from a thermally-bonded matrix predominantly comprised of synthetic fibers which maintains substantially constant resiliency and density properties even after exposure to aqueous bodily fluids. The advantageous aspects of absorbent structures of the present invention include: (a) maintenance of a comparatively low density structure to aid in handling of fluids under "gush" situations; (b) the ability to increase total fluid capacity and retain the absorbed fluid, i.e., reduce "rewet", by increasing the utilization of absorbent gelling material; and (c) reduced panty and body soiling because of the improved flexibility and resiliency of the resilient webs, even when wetted and compressed during use, and hence consistent area coverage during use. Moreover, catamenial pads, such as sanitary napkins embodying these absorbent cores and structures not only provide improved fluid handling, but also improved fit and comfort for user, especially in terms of preventing bunching of the pads during use.

8 Claims, 6 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

U.S. PATENT DOCUMENTS

| | | | |
|---|---|---|---|
| 4,980,226 | 12/1990 | Hellgren et al. | 428/218 |
| 4,988,344 | 1/1991 | Reising et al. | 604/368 |
| 4,988,345 | 1/1991 | Reising | 604/368 |
| 5,134,007 | 7/1992 | Reising et al. | 604/378 |
| 5,135,521 | 8/1992 | Luceri et al. | 604/383 |
| 5,143,779 | 9/1992 | Newkirk et al. | 428/218 |
| 5,154,714 | 10/1992 | Nomura et al. | 604/366 |
| 5,167,764 | 12/1992 | Nielsen et al. | 162/146 |
| 5,167,765 | 12/1992 | Nielsen et al. | 162/146 |
| 5,231,122 | 7/1993 | Palumbo et al. | 524/30 |
| 5,264,268 | 11/1993 | Luceri et al. | 428/138 |
| 5,300,054 | 4/1994 | Feist et al. | 604/378 |

FOREIGN PATENT DOCUMENTS

| | | |
|---|---|---|
| 0 343 940 | 11/1989 | European Pat. Off. . |
| 0 343 941 | 11/1989 | European Pat. Off. . |
| 0 359 501 | 3/1990 | European Pat. Off. . |
| 0 518 291 A1 | 12/1992 | European Pat. Off. . |
| 0 539 703 A1 | 5/1993 | European Pat. Off. . |
| 0 572 033 A2 | 12/1993 | European Pat. Off. . |
| 40 24 053 | 1/1992 | Germany . |
| 1 427 199 | 3/1976 | United Kingdom . |
| 2 168612 A | 6/1986 | United Kingdom . |
| WO 90/14061 | 11/1990 | WIPO . |
| WO 91/11162 | 8/1991 | WIPO . |
| WO 93/21881 | 11/1993 | WIPO . |
| WO 94/14397 | 7/1994 | WIPO . |
| WO 94/28838 | 12/1994 | WIPO . |

ABSORBENT STRUCTURES HAVING THERMALLY BONDED RESILIENT WEB FOR IMPROVED FIT AND COMFORT

FIELD OF THE INVENTION

The present invention relates to absorbent structures having improved resiliency and fluid handling properties. This application further relates to absorbent articles incorporating such an absorbent structure to provide improved fit and comfort during use.

BACKGROUND OF THE INVENTION

Absorbent articles come in many forms, for wearing by many different individuals in a multitude of circumstances. In the case of catamenial pads, for example, women have come to expect a high level of performance in terms of comfort and fit, retention of fluid, and minimal staining. Above all, leakage of fluid from the pad onto undergarments is regarded as totally unacceptable. Improving the performance of such catamenial pads continues to be a formidable undertaking, although a number of improvements have been made in both catamenial structures, and materials used in such structures. However, eliminating leakage, particularly along the inside of the thighs, without compromising fit and comfort, has not always met the desired needs of the consumer.

Leakage from catamenial pads, and in particular sanitary napkins, is generally attributed to a high concentration of fluid at the point where the menses exits the body and immediately contacts the surface of the napkin. At this point of deposit, the napkin absorbent structure can become quickly supersaturated. The blood migrates radially from this point and leaks from the sides nearest the wearer's legs.

The users of sanitary napkins, and the like, have also come to expect the surface of such products to provide a cleaner, more sanitary and drier aspect than common cloth or nonwoven materials have historically provided. Current sanitary napkin products are typically provided with nonwoven or formed-film permeable topsheets that are designed to move discharged menstrual fluids rapidly therethrough and into an underlyng absorbent structure. This rapid movement of acquired menstrual fluids is designed to provide a drier and cleaner surface adjacent the wearer of the product.

Prior catamenial absorbent structures, and in particular catamenial pads using such structures, have had a greater chance of causing panty and body soiling. This is because the absorbent structure lacks resilience, leading to bunching of the pad and reduced area coverage of the undergarments. This lack of resilience, and consequent bunching, has also caused these prior catamenial pads to provide poorer fit and comfort for the user.

In an effort to combat the bunching tendency, some manufacturers have incorporated a stiffening element into the absorbent structure to provide this missing resilience. Typical stiffening elements, however, in order to provide the necessary resilience usually wind up being significantly stiffer than a conventional absorbent structure and require greater forces to deform them in use. Consumer comfort, consequently, is typically sacrificed in providing resilience.

Another shortcoming of typical stiffening elements is that they are frequently manufactured from fluid-impervious materials. In order to avoid imparing the ability of the absorbent core to receive fluid and function as intended, the stiffening element must of necessity be located on the side of the absorbent structure away from the wearer. Not only does this limit structural orientation of the respective elements of the absorbent structure, but such a stiffening element is functionally inert with respect to the fluid transport and storage characteristics of the absorbent structure.

Accordingly, it would be desirable to provide absorbent structures, as well as catamenial pads embodying such structures, that provide improved resilience and integrity without sacrificing user comfort and without impairing the handling of fluids within the structure.

SUMMARY OF THE INVENTION

The present invention provides absorbent structures for absorbent articles, in particular catamenial pads, that are capable of acquiring, distributing, and storing aqueous body fluids, especially menstrual fluids, as well as providing better fit and comfort for the user of the products. These absorbent structures comprise an absorbent core and a comparatively low density, fluid-pervious, resilient web in fluid communication with the absorbent core.

The resilient webs of the present invention are formed from a thermally-bonded matrix predominantly comprised of synthetic fibers which maintains substantially constant resiliency and density properties even after exposure to aqueous bodily fluids. The resilient webs preferably maintain a comparatively low density structure to provide a built-in void volume to aid in handling of fluid under "gush" situations.

The absorbent structures of the present invention offer a number of significant advantages over prior catamenial absorbent structures. These advantages include: (a) maintenance of a comparatively low density structure to aid in handling of fluids under "gush" situations; (b) the ability to increase total fluid capacity and retain the absorbed fluid, i.e., reduce "rewet", by increasing the utilization of absorbent gelling material; and (c) reduced panty and body soiling because of the improved flexibility and resiliency of the resilient webs, even when wetted and compresses during use, and hence consistent area coverage during use. Moreover, catamenial pads, such as sanitary napkins embodying these absorbent cores and structures not only provide improved fluid handling, but also improved fit and comfort for user, especially in terms of preventing bunching of the pads during use.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

A. Definitions

Figure 1:
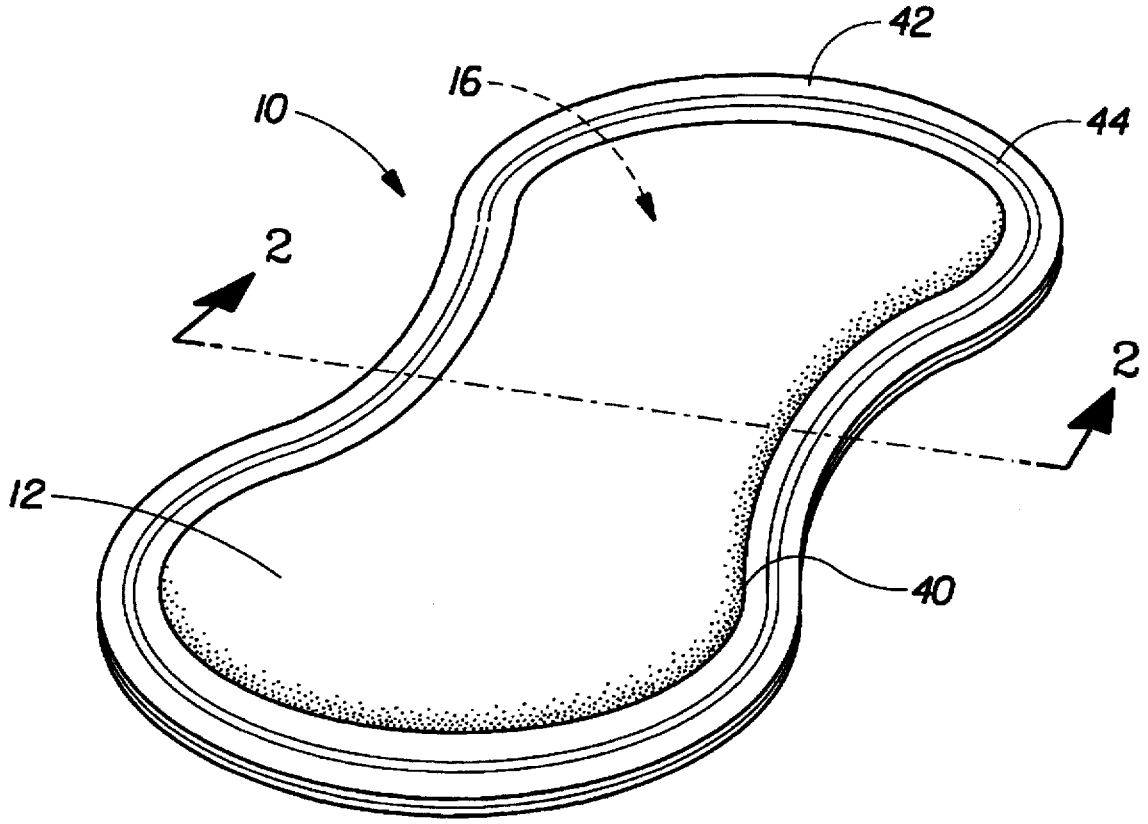
FIG. 1 is perspective view of a catamenial product having absorbent structures according to the present invention.

As used herein, the term "aqueous body fluids" includes urine, menses and vaginal discharges.

As used herein, the term "Z-dimension" refers to the dimension orthogonal to the length and width of the layer, structure, or article. The Z-dimension usually corresponds to the thickness of the layer, structure, or article.

As used herein, the term "X-Y dimension" refers to the plane orthogonal to the thickness of the layer, structure, or article. The X-Y dimension usually corresponds to the length and width of the layer, structure, or article.

As used herein, the term "comprising" means various components, layers, structures, articles, steps, and the like can be conjointly employed according to the present invention. Accordingly, the term "comprising" encompasses the more restrictive terms "consisting essentially of" and "consisting of," these latter, more restrictive terms having their standard meaning as understood in the art.

All percentages, ratios, and proportions used herein are by weight unless otherwise specified.

B. Absorbent Structure Components

1. Absorbent Core

The absorbent structures of the present invention include an absorbent core, which serves to acquire and store bodily fluids. The absorbent core itself may be of generally conventional design and composition, selected with regard to the particular application. The absorbent core may be monolayer or multilayer, homogeneous or stratified, profiled or uniform, etc. The absorbent cores may have various functional characteristics, including acquisition, distribution, and/or storage of aqueous bodily fluids. The materials useful for absorbent cores in absorbent structures according to the present invention may be natural or synthetic in origin, woven, non-woven, fibrous, cellular, or particulate, and have any other characteristics consistent with their intended functionality.

The absorbent cores may also have any desired size and/or shape as may prove suitable for a particular application, including square, rectangular, oval, elliptical, oblong, etc. They may also take on a three-dimensional shape or may be substantially planar in nature.

2. Resilient Web

The absorbent structures cores according to the present invention include an additional component not found in prior art structures. This additional component will be referred to herein as a "resilient web", by virtue of the resilient properties which this component possesses and which it imparts to the overall absorbent structure.

In terms of wearer comfort, it is imperative that the pad or absorbent article remain in a useful configuration throughout the wearing cycle. In order to do so, the absorbent article must not only retain the ability to maintain its configuration while undergoing an infusion of bodily fluids but also endure the various postures and movements of the wearer. While some absorbent structure materials may be able to do so when in their dry state, most, if not all, suffer a serious degradation of their structural integrity after infusion of bodily fluids.

Resilient webs of the present invention are able to maintain their resiliency during the course of use both in a dry state and in a wetted condition after being subjected to bodily fluids. That is to say, their performance when wet is substantially similar to their performance when dry. This unique ability to do so permits wet properties to be designed into the absorbent structure without negatively impacting consumer comfort when in the dry state. Resilient webs according to the present invention must of necessity possess resilient characteristics in both wetted and dry states without requiring excessively high compressive forces for deformation.

Resilient webs of the present invention possess the following characteristics: (1) they are pervious to fluids; (2) they have a comparatively low density in comparison with other absorbent article components; (3) they do not significantly undergo a change in density, i.e., collapse upon themselves when wet; (4) and, they exhibit what may be termed omnidirectional resiliency. Omnidirectional resiliency, as used herein, is used to refer to the ability of the resilient webs to exhibit resiliency properties in essentially all directions. Specifically, this is indicative of z-direction resiliency (compression resistance), x-y (planar) resiliency, torsional resiliency, and resiliency in a pure bending context.

In use, absorbent articles are subjected to a wide variety of stresses and strains by virtue of the motions and postures of the user. Absorbent articles are therefore subjected to compressive forces in the z and x-y directions, torsional forces, and, of course, bending forces. Resilient webs according to the present invention are able to successfully deform in response to forces in each of these orientations and to tend to return generally to their undeformed configuration both in a wet and a dry state.

An important aspect of resilient webs according to the present invention is that their compression properties are such that the addition of the web to ANY product does not significantly increase the dry or wet compression force resistance of the product. Put another way, the overall compression force properties are predominantly influenced by the other components of the product. The resilient webs do not contribute significantly to the force characteristics of the product, which would impact consumer comfort, yet they provide the needed resilience or memory to restore the product toward its undeformed configuration.

The resilient webs therefore tend to support and aid in maintaining the integrity of the entire absorbent structure. This is particularly important when the remainder of the absorbent structure (in particular, the absorbent core) consists of materials not having inherent integrity characteristics, such as cellulosic materials (commonly referred to as "airfelt"). Even in the event that core integrity is lost, and the absorbent core begins to disintegrate or shift within the absorbent article, the resilient web will tend to maintain its initial configuration and orientation, providing at least some measure of fluid handling capability rather than allowing the backsheet of the absorbent article to be directly exposed to incoming fluid.

Importantly, since the resilient webs are pervious to fluids, while not exhibiting significant storage capabilities the resilient webs are able to participate in the handling of the incoming fluids and enhance the performance of other components of the absorbent structure. Because the resilient web is a generally comparatively low density structure, the inclusion of such resilient web builds in a certain amount of void volume within the absorbent structure. As used herein, the term "comparatively low density" is used to refer to materials having a density on the order of, for example, less than about 0.07 g/cc under a confining pressure of 0.29 psi.

Because the resilient web is able to maintain its comparatively low density under compressive forces, well as other distortions, and to resist permanent deformation this void volume is maintained under a wide variety of in-use conditions. Built in void volume, in turn, assists in the handling of fluid under "gush" situations, where fluid enters the absorbent article faster than the remainder of the absorbent core and process, distribute, and store it.

Another benefit of the utilization of the resilient webs of the present invention is the ability to more effectively utilize absorbent gelling material in the storage layer. Because of gel blocking and poor fluid transport of menses, the level of absorbent gelling material that can be included in prior catamenial absorbent structures is limited and overall utilization is less than desirable. By contrast, the absorbent structures according to present invention permit the absorbent gelling material to be more effectively utilized, resulting in an increased overall storage capacity per unit volume.

This increased utilization efficiency is realized when resilient webs according to the present invention are located within the absorbent structure where they are immediately adjacent to a layer containing the absorbent gelling material. As such materials expand when they acquire fluid, the comparatively low density structure of the resilient web allow a degree of "free space" for the gelling material to expand or swell into. In effect, the absorbent gelling material is cushioned by the presence of the comparatively low density, resilient web during various in-use conditions rather than the more restrictive and confining, comparatively higher density structures typically adjacent to such layers. This in turn combats the tendency of absorbent gelling material particles to swell into contact with one another due to the confined space and a corresponding restriction on the ability of the material to expand and acquire fluid.

Since resilient webs according to the present invention are fluid-pervious, rather than being fluid-impervious, the resilient web need not be located on the farthest side of the absorbent article from the source of the incoming fluid. Indeed, the resilient web according to the present invention may be included within the absorbent structure in a location above at least some of the absorbent core structure. The resilient web could also be included on the side of the absorbent structure facing the incoming fluid. It is presently preferred that the resilient webs according to the present invention be located above at least some of the absorbent core structure so that the void volume capabilities of the resilient web may participate in the fluid handling properties of the absorbent structure. In cases where the absorbent core consists of multiple layers such as two, three, or four layers, the resilient web may be located between any two layers of the absorbent core.

The manner in which the resilient web is integrated into/joined with the remaining components of the absorbent structure does have an impact upon the role the resilient web plays in determining the physical characterics of the structure as a whole. Depending upon its location within the absorbent structure, it may be desirable to secure one or both sides of the resilient web to one or more adjacent layers/structures to maintain its orientation and/or to aid in the imparting of its resilient properties to the adjoining structures. Suitable methods of securement include, for example, gluing with adhesives, thermal bonding, ultrasonic bonding, compression bonding, and mechanical fastening. Of these, the use of adhesives is the presently preferred bonding method. Even in circumstances where a specific bonding method or mechanism is not utilized, mechanical factors such as surface friction and fiber entanglement between the resilient web and adjoining structures will to at least some degree aid in the providing of resilient properties to the structure as a whole.

The resilient webs according to the present invention may also have any desired size and/or shape as may prove suitable for a particular application, including square, rectangular, oval, elliptical, oblong, etc. They may also take on a three-dimensional shape or may be substantially planar in nature. Further, they may have a size and shape complementary to the absorbent core and/or the remainder of the absorbent structure, or may have a different shape and/or size. Accordingly, the resilient web may be smaller or larger than the absorbent core in one or more dimensions, and may be disposed in relation to the core such that it only interacts with a specific portion or zone of the core, or may be substantially coextensive with the core.

The physical properties and characteristics of the resilient web in terms of omnidirectional resiliency are detailed further below in terms of the physical properties and the methods for determining these physical properties.

C. Composition of Resilient Web

The resilient web of the present invention preferably comprises the following components:

1. Thermoplastic Material

Resilient webs according to the present invention preferably comprise thermoplastic fibrous material. Upon melting, at least a portion of this thermoplastic material migrates to the intersections of the fibers, typically due to interfiber capillary gradients. These intersections become bond sites for the thermoplastic material.

When cooled, the thermoplastic material at these intersections solidify to form the bond sites that maintain the structure of the web or matrix of fibers to create the desired level of compression resistance, resilience, and density. Note that although the term "melting" is commonly used in the art, a more accurate term might be "softening", as the thermoplastic material is not truly melted to the point of liquification but merely to the point where the outermost surface of the thermoplastic fibers begins to soften and become tacky.

Amongst its various effects, bonding at these fiber intersections increases the overall compressive modulus and strength of the resulting thermally bonded matrix. This can improve the fluid acquisition properties of the thermally bonded layer upon initial discharges, due to improved fluid permeability, and upon subsequent discharges, due to the ability of the thermoplastic material to resist the effects of moisture and remain bonded at the fiber intersections upon wetting and upon wet compression.

Thermoplastic materials useful in the present invention can be in any of a variety of forms including particulates, fibers, or combinations of particulates and fibers. Thermoplastic fibers are a particularly preferred form because of their ability to form numerous interfiber bond sites. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in absorbent articles, are likely to be stored. The melting point of the thermoplastic material is typically no lower than about 50° C.

The thermoplastic materials, and n particular the thermoplastic fibers, can be made from a variety of thermoplastic polymers, including polyolefins such as polyethylene (e.g., PULPEX®) and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the foregoing such as vinyl chloride/vinyl acetate, and the like. Depending upon the desired characteristics for the resulting thermally bonded matrix, suitable thermoplastic materials include hydrophobic fibers that have been made hydrophilic, such as surfactant-treated or silica-treated thermoplastic fibers derived from, for example, polyolefins such as polyethylene or polypropylene, polyacrylics polyamides polystyrenes, polyurethanes and the like. The surface of the hydrophobic thermoplastic fiber can be rendered hydrophilic by treatment with a surfactant, such as a nonionic or anionic surfactant e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, for about 0.2 to about 1 g. per sq. centimeter of thermoplastic fiber.

The ability to tailor (i.e., enhance) the wettability of the thermoplastic fibers utilized in the resilient web is particularly important for resilient webs which are incorporated into the absorbent structure in a location between the source of the fluid and a portion of the fluid storage structure. If the resilient web were to remain substantially hydrophobic, the capacity of the portion of the absorbent core lying below the resilient web would not be utilized due to the shielding action of the resilient web.

Suitable thermoplastic fibers can be made from a single polymer (monocomponent fibers), or can be made from more than one polymer (e.g., bicomponent fibers). As used herein, the term "bicomponent fibers" refers to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp. Eccentric bicomponent fibers can be desirable in providing a lower density structure due to the greater tendency of such fibers (in comparison with concentric bicomponent fibers) to take on a curled or "kinked" shape due to the differing properties of the eccentrically oriented core and sheath materials.

The bicomponent fibers presently preferred for use in the resilient webs according to the present invention are formed using a hydrophilic resin from Dow Chemical called ASPUN (CODE XU 61518.11), which is a polyethylene resin containing a wetting agent, of the type described in U.S. Pat. No. 4,578,414. Polyethylene itself is inherently hydrophobic. Bicomponent crimped fibers are formed incorporating this wettable resin. The fibers comprise a polypropylene core and a sheath which is formed of the wettable resin mixed with LLDPE (linear, low density polyethylene). At least a portion of the surface of the core is exposed to the exterior of the fiber to form an eccentric fiber configuration as described above. The fibers are thus rendered predominantly hydrophobic. A spin finish coating, Chisso HR5, is applied to the fibers for processing and to impart hydrophilicity. The fibers are cut into staple fibers 6 mm in length, and the staple fibers are airlaid to form a resilient web of wholly synthetic, hydrophilic fibers. The fibers have a diameter of about 18 μm. The process of airlaying includes the step of applying heat or an adhesive to cause those fibers which touch, or almost touch, one another to bond to each other and those points.

In the case of bicomponent thermoplastic fibers, their length can vary depending upon the particular properties desired for these fibers. Typically, these thermoplastic fibers have a length from about 0.3 to about 7.5 cm long, preferably from about 0.4 to about 3.0 cm long, and most preferably from about 0.5 to about 1.2 cm long. The properties-of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers can have a decitex in the range from about 1.0 to about 20, preferably from about 1.4 to about 10, and most preferably from about 1.7 to about 7.0.

The compressive modulus of resilient webs made of these bonded thermoplastic fibers can also be important. The compressive modulus of the web is affected not only by the length and diameter of the fibers, but also by the composition and properties of the polymer or polymers from which they are made, the shape and configuration of the fibers (e.g., concentric or eccentric, crimped or uncrimped), and like factors. Different in the compressive modulus of these thermoplastic fibers can be used to alter the properties, and especially the density characteristics, of the respective thermally bonded fibrous matrix.

2. Optional Synthetic Fibers

The resilient web according to the present invention can optionally comprise some synthetic fibers that typically do not function as binder fibers but alter the mechanical properties of the fibrous webs. Such fibers, although often thermoplastic, may not participate in the bonding process due to their having a higher melting or softening point than the binder fibers, although under some circumstances their participation may be desirable. Suitable synthetic fibers for use in the present invention include polyester fibers such as polyethylene terephthalate (e.g., DACRON® and KODEL®), high melting crimped polyester fibers (e.g., KODEL® 431 made by Eastman Chemical Co.) hydrophilic nylon (HYDROFIL®), and the like. Suitable fibers can also be hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length can vary depending upon the particular properties desired for these fibers. Typically they have a length from about 0.3 to 7.5 cm, preferably form about 0.9 to about 1.5 cm. Suitable nonbonding thermoplastic fibers can have a decitex in the range of about 1.5 to about 35 decitex, more preferably from about 14 to about 20 decitex.

3. Other Materials

For certain applications, it may be desirable to include other, non-thermoplastic materials in the resilient web, in order to "fine tune" the mechanical properties of the resilient web. An example of such a material is cellulosic fibers (commonly referred to as "airfelt"), commonly available under such trade names as "Flint River Fluff" or Weyerhauser NB416, although non-organic materials such as absorbent gelling materials in fibrous or non-fibrous form could also be utilized. Such organic materials, if present, are preferably present in a minor amount such that the ability of the resilient web to maintain a wet resiliency substantially equal to its dry resiliency are not significantly affected.

4. Preparation of Resilient Web from Thermally Bonded Layers a. Forming Layers from Mixtures of Fibers and Thermoplastic Material The thermally bonded layers of the absorbent core are formed from thermoplastic material previously described, plus any optional components such as hydrophilic synthetic fibers. The thermoplastic material is typically evenly distributed throughout the web or matrix of fibers in each layer, i.e. the composition of each fibrous layer is substantially homogeneous. This not only assures adequate interfiber bonding of this fibrous web/matrix, but also insures that the resulting fibrous layer has a substantially uniform density when subjected to subsequent thermal bonding and densification.

The particular amount of thermoplastic material within this mixture for each layer depends upon a number of factors, including the degree of thermal bonding desired, the particular fibers and thermoplastic material used, the particular density or other properties desired for the resulting thermally bonded layer, and like factors. In order to obtain the resiliency properties of the present invention, the resilient webs are preferably comprised of a predominantly synthetic fibrous material, with at most a minor amount of natural cellulosic or other non-synthetic fibrous material. Accordingly, resilient webs according to the present invention preferably comprise at least about 50% (a majority) synthetic material, more preferably at least about 75% synthetic material, and most preferably, about 100% synthetic material.

Of the proportion of synthetic material, the composition may include various amounts of thermoplastic material depending upon the desired physical properties. The overall proportion of synthetic materials, including thermoplastics, is a significant determining factor in controlling z-direction compressive resistance (crush) and maintenance of wet properties, while the proportion of thermoplastic materials is a significant determining factor in controlling other resilient properties such as resistance to x-y compression, torsion, and bending forces. Accordingly, resilient webs according to the present invention preferably comprise at least about 10% thermoplastic bicomponent fibers, more preferably at least about 75% thermoplastic bicomponent fibers, and most preferably, about 100% thermoplastic bicomponent fibers.

The thermoplastic material can be formed into layers by any of a variety of techniques, including wet-laying methods and air-laying methods, as well as carding and other methods.

More typically, each fibrous layer of the absorbent structure according to the present invention is formed by air-laying the mixture of fibers and thermoplastic material. In general, air-laying can be carried out by metering an airflow containing the fibers and thermoplastic material, in substantially dry condition, onto a typically horizontally moving wire forming screen. Suitable systems and apparatus for air-laying mixtures of fibers and thermoplastic material are disclosed in, for example, U.S. Pat. No. 4,157,724 (Persson), issued Jun. 12, 1979, and reissued Dec. 25, 1984 as Re. 31,775; U.S. Pat. No. 4,278,113 (Persson), issued Jul. 14, 1981; U.S. Pat. No. 4,264,289 (Day), issued Apr. 28, 1981; U.S. Pat. No. 4,352,649 (Jacobsen et al), issued Oct. 5, 1982; U.S. Pat. No. 4,353,687 (Hosler et al), issued Oct. 12, 1982; U.S. Pat. No. 4,494,278 (Kroyer et al), issued Jan. 22, 1985; U.S. Pat. No. 4,627,806 (Johnson), issued Dec. 9, 1986; U.S. Pat. No. 4,650,409 (Nistri et al), issued Mar. 17, 1987; and U.S. Pat. No. 4,724,980 (Farley), issued Feb. 16, 1988, all of which are incorporated by reference.

A particularly desirable system for air-laying thermoplastic material according to the present invention is disclosed in U.S. Pat. No. 4,640,810 (Laursen et al), issued Feb. 3, 1987, which is incorporated by reference. In this system, the thermoplastic material supported in an airstream and introduced into a distributor unit. This distributor unit includes one or more rotatable cylindrical drums formed with classification apertures of predetermined shape, number and size as specifically related to the types of fibers and thermoplastic material utilized. To accept flows of relatively short fibers, or thermoplastic material in particulate form, these apertures are preferably circular and have a diameter substantially equivalent to the length or size of the fibers and/or particles introduced into the system, and are large in number per unit length of the drum. To accept flows of relatively long fibers, or blends of long and short fibers and/or particles, these apertures are preferably rectangular in configuration with a length generally twice that of the long fibers and a width generally ten times the diameter of these fibers. Because the rectangular apertures are larger than the circular apertures, their number is moderate per length of the drum in comparison to the circular apertures.

Each of the cylindrical drums has within it a shaft with radially extending wire-like members that is rotated in a direction opposite that of the associated drum. The wire-like members engage the individual fibers and/or particles and fling them through the apertures in the drum. Simultaneously, the wire-like members agitate the fibers and/or particles to maintain a homogeneous mixture thereof. A downwardly directed airflow then transports this homogeneous-airborne mixture onto a typically horizontally moving foraminous carrier so as to form a layer of fibers and/or particles of substantially uniform composition. Alternatively, if desired, the fibrous layer could be formed with a density gradient in the thickness direction.

In some cases, it can be desirable to provide integrated absorbent structure and/or cores. To provide such integrated structures and/or cores two or more air-laying heads are used to laydown the respective layers sequentially. Absorbent gelling material for the storage layer (with or without a carrier) can be added between the appropriate air-laying heads to provide integrated, laminate absorbent cores, or may be integrated homogeneously into one or more layers by entraining the particles into the fiber stream.

The thermoplastic material for layers of the absorbent structure can be formed separately and then combined later after thermal bonding/densification. Alternatively, if an integral absorbent structure is desired, the resilient web, as well as one or more of the other layers in the absorbent structure can be formed at the same time. In forming those these integral thermally bonded absorbent structures, one of the layers is formed from the thermoplastic material. The subsequent layers are also formed and then combined with the first layer. It should be understood that the formation of the respective layers and their combination could occur in any order and in any number of orientations, including horizontal and vertical planes. In particular, it should be understood that formation of the first layer need not be completed prior to the start of formation of the subsequent fibrous layers. Indeed, the first layer need only be partially formed prior to the start of formation of the subsequent fibrous layers. Typically, the subsequent layers are formed by depositing them on top of a complete, or only partially formed, first layer that is oriented horizontally.

b. Thermal Bonding and Densification of Combined Layers

After the layer, or in the case of integral absorbent structures, layers are formed, they are thermally bonded and then typically densified. Thermal bonding and densification of the layer or layers can occur in a number of different orders. For example, densification of the fibrous layer(s) can occur prior to thermal bonding, during thermal bonding and/or after thermal bonding. The particular order in which these densification and thermal bonding steps occur will often depend upon the particular fibers and thermoplastic material present in the respective fibrous layers(s), the particular properties desired in the resulting thermally bonded layer(s), especially the particular density characteristic desired, and like factors.

Densification of the fibrous layer(s) is usually carried out by the application of pressure. For example, in the case of air-laid layers, compressive forces are typically applied to the opposed surfaces of the layer. Such compressive forces can be applied by using opposed platens, or more typically by the use of opposed rollers. Preferably, a pair of opposed calender rolls are used to apply compressive forces to the air-laid layer(s).

Thermal bonding of the formed layer(s) can be carried out by any of a variety of techniques. For example, in the case of air-laid layers, thermal bonding is typically achieved by heating the formed layer(s) above the melt point of the thermoplastic material present therein. Air-laid layers are typically heated to temperatures in the range from about 70° C. to about 190° C., preferably from about 100° C. to about 160° C., and most preferably from about 120° C. to about 150° C. The particular temperature to which the layer is heated will depend upon a number of factors, including the melt point of the thermoplastic material present in the fibrous layer, the particular properties desired in the resulting thermally bonded fibrous matrix, and like factors.

The formed layer(s) can be heated by any of a variety of techniques. One such technique involves heating the formed layer(s) while it is being subjected to compressive forces required for densification. For example, the formed layer(s) can be passed between a pair of opposed calender rolls, one or both of which have been heated to the appropriate temperature. A particularly suitable technique for heating air-laid layers is by passing them through a hot-air oven in the absence of the application of compressive forces.

c. Post Processing

If desired, the resilient webs of the present invention may be subjected to any one of a number of what may be termed generically as "post processing techniques" after formation to further tailor the desired mechanical properties. Such techniques include creping, embossing, mechanically straining via corrugated rolls, spot bonding, gluing, etc. By creating particular patterns of greater or lesser resilience, the performance attributes of the resilient web, and hence the absorbent structure, may be altered in any one or more orientation.

d. Preferred Thermally Bonded Materials and Methods for Making Same

The resilient webs of the present invention are preferably air laid using an air laying head similar to that disclosed in U.S. Pat. No. 4,640.810 (Laursen et al), issued Feb. 3, 1987, which is incorporated by reference. The fibrous materials are deposited from one or more air laying heads at a weight of about 10 to about 200 grams per square meter (gsm). A defibrator is used (if cellulosic materials are to be included) to separate the fibers of dry-lap into individual fibers which are blended into an air stream that is fed to the air laying heads. After the fibrous materials are laid down and combined to form a web, they go through an oven that softens the outer coating (sheath) of the binding fibers (in the case of bicomponent fibers; otherwise, the outer surface of single component fibers). The oven temperature is typically set so the binding fibers are at a temperature above the melt point of the sheath but below that of the core. The over temperature may also be tailored to match the desired line speed and oven length, such that the fibers reach their melt (softening) point during the residence time of any particular segment of the web in the oven.

The web can be compressed before and/or after the oven to achieve the desired dry and/or wet density. A density gradient either in the z-direction or in the x-y plane may be incorporated into the resilient web by tailoring the rate of fiber deposition, although a substantially uniform density profile throughout the resilient web is generally preferred. The final web is then cooled to set the bonds between fibers.

5. Physical Properties of Resilient Web a. Wet and Dry Caliper

The caliper or thickness of the resilient web is selected according to the desired overall thickness of the absorbent structure, and hence the absorbent article, as well as the degree of resiliency to be imparted to the absorbent structure. Caliper measurements are obtained by measuring the thickness of a single layer of the material, i.e. a single resilient web, under a given confining pressure for consistency. Typical calipers of resilient webs useful in the present invention are on the order of about 1 mm to about 4 mm under a confining pressure of 0.06 psi., although calipers of greater or lesser dimension are contemplated if desired.

b. Dry Density

The dry density of the resilient web, in combination with the dry caliper, define the basis weight of the resilient web. For a given resilient material, the dry density is determinative of the wet density and hence is the baseline for defining the material properties. Dry densities, like calipers, are measured under a particular confining pressure. Typical dry densities of resilient webs useful in the present invention are preferably no greater than 0.07 g/cc under a confining pressure of 0.29 psi., and are preferably on the order of 0.01–0.04 g/cc under a confining pressure of 0.06 psi.

c. Wet Density

The wet density of the resilient web has been found to have an important effect on the fluid uptake capacity and efficiency of the absorbent gelling material (AGM). As discussed above, it is desirable to have a comparatively low density structure, i.e., resilient web, adjacent to an AGM-containing structural element to provide for a cushioning effect and allow for expansion of the AGM.

In order to provide the desired cushioning effect under in-use conditions, it is desirable that the density of the resilient web when in a wetted condition remain substantially similar to the dry density of the web under comparable confining pressures. Accordingly, resilient webs according to the present invention preferably exhibit a wet density of at least about 80% of the dry density, more preferably at least about 90%, and most preferably about 100% of the dry density under comparable confining pressures.

d. Wet Compression

The quantity termed "wet compression" is a reflection of how well the dry and wet densities correlate in the resilient web. Wet compression at a given confining pressure is defined as $$\text{Wet compression}=100\times((\text{wet density}+\text{dry density})-1)$$

Corresponding to the wet density ranges discussed above, resilient webs according to the present invention preferably exhibit a wet compression of less than about 20%, more preferably less than about 10%, and most preferably about 0%. At the limiting condition where wet density would equal dry density, the wet compression would therefore equal zero.

The dry caliper, wet caliper, dry density, wet density, and wet compression properties (at given confining pressures) of a representative thermally bonded material useful as a resilient web in the present invention are shown in Table 1 below:

TABLE 1

| Confining Pressure (psi) | 0.06 | 0.29 |
|---|---|---|
| Dry caliper (in.) | 0.083 | 0.060 |
| Wet caliper (in.) | 0.084 | 0.063 |
| Dry density (g/cc) | 0.0249 | 0.0344 |
| Wet density (g/cc) | 0.0271 | 0.0360 |
| Wet compression | 8.8% | 4.7% |

D. Catamenial Pads, Sanitary Napkins and Related Absorbent Articles

1. Exemplary Embodiments

A preferred embodiment of a catamenial pad or sanitary napkin 10 according to the present invention is shown in FIG. 1. As used herein, the term "sanitary napkin" refers to an absorbent article that is worn by females adjacent to the pudendal region, generally external to the urogenital region, and which is intended to absorb and contain menstrual fluids and other vaginal discharges from the wearer's body (e.g., blood, menses, and urine). Interlabial devices that reside partially within and partially external of the wearer's vestibule are also within the scope of this invention. As used herein, the term "pudendal" refers to the externally visible female genitalia. It should be understood, however, that the present invention is also applicable to other feminine hygiene or catamenial pads such as pantiliners, or other absorbent articles such as incontinence pads, and the like.

Absorbent structures according to the present invention typically include a fluid acquisition layer. This fluid acquisition layer is commonly referred to in the catamenial art as a "secondary topsheet". The purpose of the secondary topsheet is to rapidly draw discharged aqueous body fluids, in particular menstrual fluids, through the adjacent permeable (primary) topsheet. This allows the surface of the primary topsheet adjacent the wearer of the catamenial pad to remain relatively clean and dry.

Figure 2:
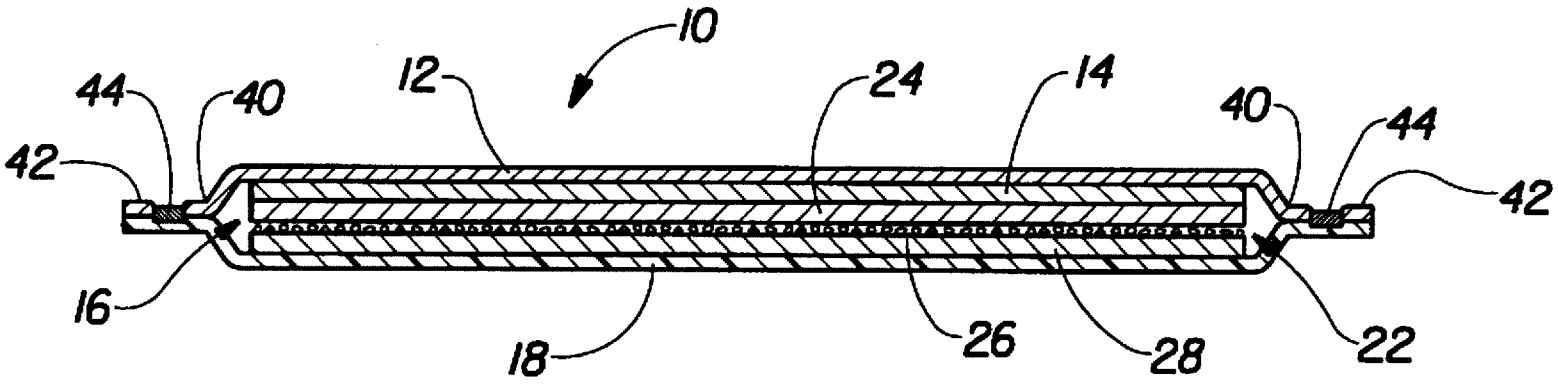
FIG. 2 is a cross-sectional view take along line 2—2 of FIG. 1.

As best seen from FIG. 2, catamenial pad 10 is constructed of fluid pervious primary topsheet 12, a fluid acquiring (optional) secondary topsheet 14, an absorbent structure indicated generally as 16, and fluid impervious backsheet 18. The backsheet 18 and the topsheet 12 are positioned adjacent the garment surface and the body surface, respectively, of pad 10 and are preferably joined to each other. For example, the backsheet 18 and the topsheet 12 can be secured to each other by adhesive. Adhesives that have been found to be satisfactory are manufactured by H. B. Fuller Company of St. Paul, Minn. under the designation HL-1258 or H-2031. Alternatively, topsheet 12 and backsheet can be joined to each other by heat bonding, pressure bonding, ultrasonic bonding, dynamic mechanical bonding, or any other suitable method for joining topsheets and backsheets known in the art.

A particularly suitable method for joining topsheet 12 and backsheet 18 together is by a crimp seal. As shown in FIG. 1, the lateral edges of absorbent structure 16 define a perimeter 40. The primary topsheet 12 and backsheet 18 each have a shape similar to, but larger than, absorbent structure 16. Thus, topsheet 12 and backsheet 18 each have a portion that extends outwardly from perimeter 40 of the absorbent structure 16 to define a continuous border segment that encircles the absorbent structure. Border segment 42 is generally relatively narrow, and can extend a distance of approximately 0.25 to 6 mm. and preferably is approximately 3 mm. wide. However, the width of border 42 can be uniform or vary about the perimeter of pad 10. Moreover, border segment 42 is relatively thin and flexible and is intended to provide improve protection against soiling of the vicinity surrounding the discharge region.

A fluid impermeable seal 44 is provided in border segment 42 that surrounds perimeter 40. Thus, seal 4 is adapted to prevent lateral migration (i.e., "wicking") of fluid from perimeter 40 of absorbent structure 16 through border segment 42 toward the peripheral edges of catamenial pad 10, thereby inhibiting premature side soiling of the wearer's undergarments. As a result, topsheet 12 and backsheet 18, tend to remain relatively free of fluids. Seal 44 is preferably disposed laterally inwardly as close as possible to perimeter 40 so that a greater portion of border segment 42 remains dry and unsoiled. Seal 44 preferably completely surrounds perimeter 40 without any gaps that would allow wicking and fluid leakage.

Seal 44 is preferably formed by the simultaneous application of pressure, with or without heat, commonly referred to as a "crimping" operation. During the "crimping" process, sufficient pressure, optionally with heat, is applied to melt topsheet 12 and backsheet 18, thereby forming seal 44. Portions of border 42 outside of seal 44 are crimped with discrete spaced-apart bonds. This discrete bonding creates a reverse or negative capillary gradient so that any fluids inadvertently passing through seal 44 will tend to be attracted toward the more dense material in the area of seal 44; any fluid movement outside seal 44 occurs along seal 44, as opposed to toward outer edge of border 42.

One presently preferred embodiment of an absorbent structure 16 according to the present invention used in catamenial pad 10 is shown in FIG. 2. As shown in FIG. 2, this particular absorbent structure 16 comprises an absorbent core 22 in fluid communication with the secondary topsheet 14 and a resilient web 28. If desired, the secondary topsheet can be joined to the absorbent core by a suitable adhesive, or by other types of bonding such as thermal bonding.

Absorbent core 22 is shown in FIG. 2 as comprising two components: a fluid distribution layer 24 and a fluid storage layer 26. The distribution layer 24 and the storage layer 26 are preferably formed separately and then adhesively bonded together, although they could be integrally formed if desired. The storage layer 26 also preferably includes a quantity of absorbent gelling material homogeneously distributed throughtout. Although it is possible to join resilient web 28 and distribution layer 26 through other methods, as described above, the absorbent core and resilient web are preferably joined together by the use of adhesives.

Figure 3:
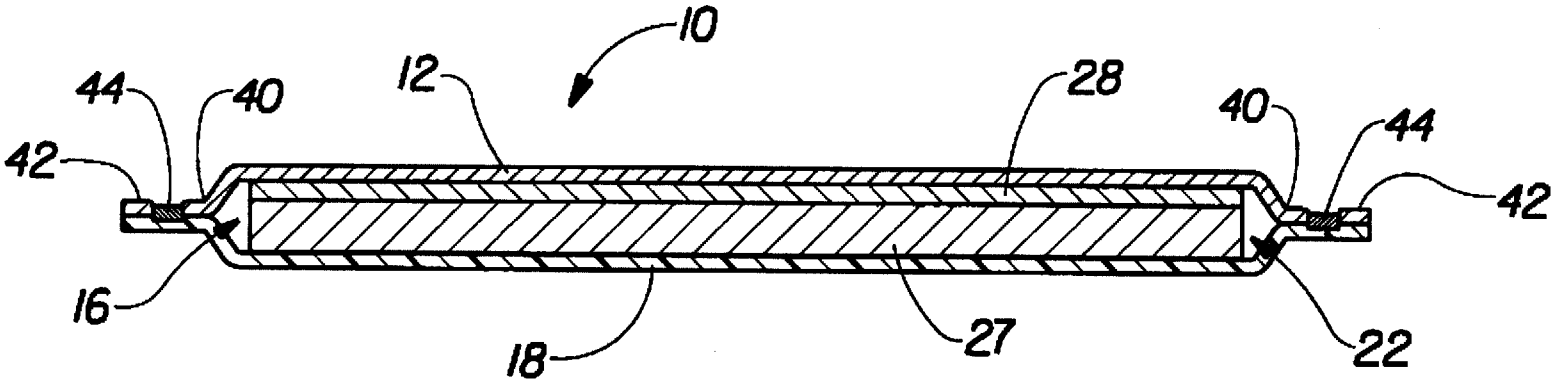
FIG. 3 is a cross-sectional view showing an alternative absorbent structure according to the present invention.

FIG. 3 shows another embodiment according to the present invention. Like the embodiment shown in FIG. 2, absorbent structure 16 of FIG. 3 comprises an absorbent core 22 and a resilient web 28. Unlike the embodiment shown in FIG. 2, the absorbent core 22 of FIG. 3 comprises one generic component: fluid storage layer 27. The absorbent structure 16 of FIG. 3 provides resilience characteristics similar to those of the embodiment of FIG. 2, and in addition moves the built-in void space provided by the resilient web above the absorbent core as may be desirable with certain absorbent core structures. The fluid storage layer 27 depicted in FIG. 3 is intended to truly generically represent a fluid handling member, and may in fact comprise one of more layers of any desired construction, composition, and functionality.

Figure 4:
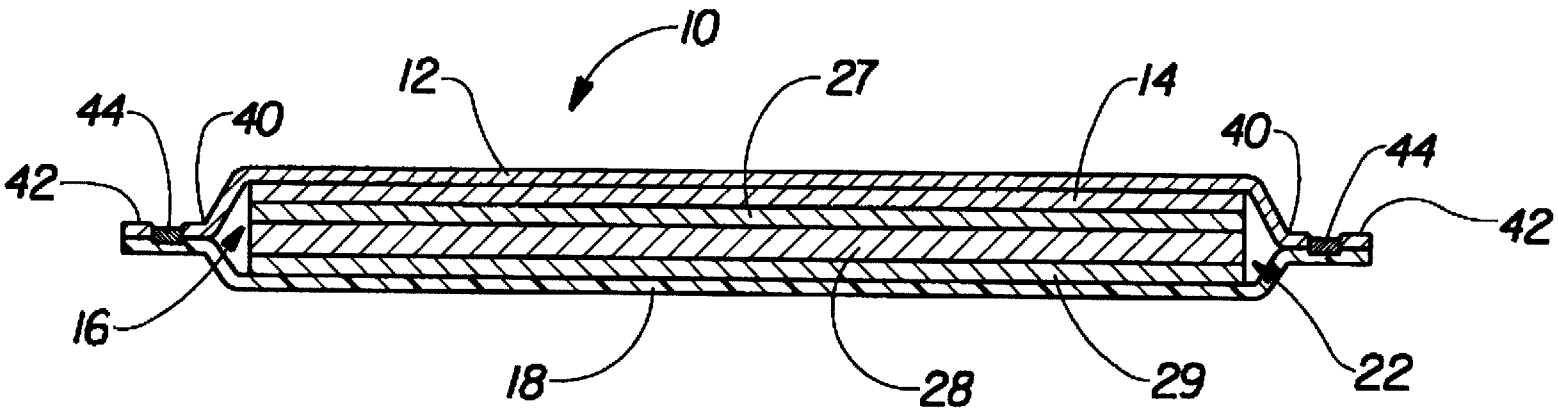
FIG. 4 is a cross-sectional view showing an alternative absorbent structure according to the present invention.

FIG. 4 shows another embodiment according to the present invention. Like the embodiment shown in FIG. 2, absorbent structure 16 of FIG. 4 comprises a secondary topsheet 14, an absorbent core 22, and a resilient web 28. Unlike the embodiment shown in FIG. 2, the absorbent core 22 of FIG. 4 comprises two generic components: fluid storage layers 27 and 29. The absorbent structure 16 of FIG. 4 provides resilience characteristics similar to those of the embodiment of FIG. 2, and in addition moves the built-in void space provided by the resilient web up into the absorbent core as may be desirable with certain absorbent core structures. The fluid storage layers 27 and 29 depicted in FIG. 4 are intended to truly generically represent fluid handling members, and each may in fact comprise one or more layers of any desired construction, composition, and functionality.

The backsheet 18 is impervious to liquids (e.g., menses and/or urine) and is preferably manufactured from a thin plastic film, although other flexible liquid impervious materials may also be used. As used herein, the term "flexible" refers to materials that are compliant and will readily conform to the general shape and contours of the human body. The backsheet 18 prevents the exudates absorbed and contained in the absorbent core 22 from wetting articles that contact the sanitary napkin 10 such as pants, pajamas and undergarments. The backsheet 18 can comprise a woven or nonwoven material, polymeric films such as thermoplastic films of polyethylene or polypropylene, or composite materials such as a film-coated nonwoven material. Preferably, the backsheet is a polyethylene film having a thickness of from about 0.012 mm (0.5 mil) to about 0.051 mm (2.0 mils). Exemplary polyethylene films are manufactured by Clopay Corporation of Cincinnati, Ohio, under the designation P18-0401 and by Tredegar Film Products, Visqueen Film Division, of Terre Haute, Ind., under the designation XP-39385. The backsheet is preferably embossed and/or matte finished to provide a more clothlike appearance. Further, the backsheet 18 can permit vapors to escape from the absorbent structure 16 (i.e., breathable) while still preventing exudates from passing through the backsheet 18.

The topsheet 12 is compliant, soft feeling, and non-irritating to the wearer's skin. Further, the topsheet 12 is fluid pervious permitting fluids (e.g., menses and/or urine) to readily penetrate through is thickness. A suitable topsheet 12 can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester polypropylene, or polyethylene fibers) or from a combination of natural and synthetic fibers.

Preferred topsheets for use in the present are selected from high loft nonwoven topsheets and aperture formed film topsheets. Apertured formed films are especially preferred for the topsheet because they are pervious to body exudates and yet non-absorbent and have a reduced tendency to allow fluids to pass back through and rewet the wearer's skin. Thus, the surface of the formed film that is in contact with the body remains dry, thereby reducing body soiling and creating a more comfortable feel for the wearer. Suitable formed films are described in U.S. Pat. No. 3,929,135 (Thompson), issued Dec. 30, 1975; U.S. Pat. 4,324,246 (Mullane, et al.), issued Apr. 13, 1982; U.S. Pat. No. 4,342,314 (Radel. et al.), issued Aug. 3, 1982; U.S. Pat. No. 4,463,045 (Ahr et al.), issued Jul. 31, 1984; and U.S. Pat. No. 5,006,394 (Baird) issued Apr. 9, 1991. Each of these patents are incorporated herein by reference. Particularly preferred microapertured formed film topsheets are disclosed in U.S. Pat. No. 4,609,518 (Curro et al), issue Sep. 2, 1986 and U.S. Pat. No. 4,629,643 (Curro et al), issued Dec. 16, 1986, which are incorporated by reference. The preferred topsheet for the present invention is the formed film described in one or more of the above patents and marketed on sanitary napkins by The Procter & Gamble Company of Cincinnati, Ohio as "DRI-WEAVE."

The body surface of the formed film topsheet can be hydrophilic so as to help liquid to transfer through the topsheet faster than if the body surface was not hydrophilic so as to diminish the likelihood that menstrual fluid will flow off the topsheet rather than flowing into and being absorbed by the absorbent structure. In a preferred embodiment, surfactant is incorporated into the polymeric materials of the formed film topsheet such as is described in U.S. patent application Ser. No. 07/794,745, "Absorbent Article Having A Nonwoven and Apertured Film Coversheet" filed on Nov. 19, 1991 by Aziz, et al., which is incorporated by reference. Alternatively, the body surface of the topsheet can be made hydrophilic by treating it with a surfactant such as is described in the above referenced U.S. Pat. No. 4,950,254, incorporated herein by reference.

In use, pad 10 can be held in place by any support or attachment device (not shown) well-known for such purposes. Preferably, pad 10 is placed in the user's undergarment or panty and secured thereto by a fastener such as an adhesive. The adhesive provides a means for securing the pad in the crotch portion of the panty. Thus, a portion or all of the outer surface of the backsheet 18 is coated with adhesive. Any adhesive or glue used in the art for such purposes can be used for the adhesive herein, with pressure-sensitive adhesives being preferred. Suitable adhesives are Century A-305-IV manufactured by the Century Adhesives Corporation of Columbus, Ohio; and Instant Lock 34-2823 manufactured by the National Starch and Chemical Company of Bridgewater, N.J. Suitable adhesive fasteners are also described in U.S. Pat. No. 4,917,697. Before pad 10 is placed in use, the pressure-sensitive adhesive is typically covered with a removable release liner in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. Non-limiting examples of suitable release liners are BL30MG-A Silox E1/0 and BL30MG-A Silox 4P/O both of which are manufactured by the Akrosil Corporation of Menasha, Wis. The pad 10 is put in use by removing the release liner and thereafter placing the pad in a panty so that the adhesive contacts the panty. The adhesive maintains the pad 10 in its position within the panty during use.

2. Physical Properties of Absorbent Articles Containing Resilient Webs

The absorbent structures according to the present invention have also been to impart physical properties to catamenial products that go beyond the ability to acquire, distribute and store fluids. When worn, catamenial pads and other related catamenial products are subjected to lateral compression forces. When these compressive forces are released, the pad then rebounds from its compressed state.

An important aspect of resilient webs according to the present invention is that their compression properties are such that the addition of the web to ANY product does not significantly increase the dry or wet compression force resistance of the product. Put another way, the overall compression force properties are predominantly influenced by the other components of the product. The resilient webs do not contribute significantly to the force characteristics of the product, which would impact consumer comfort, yet they provide the needed resilience or memory to restore the product toward its undeformed configuration.

How the pad reacts to these compressive forces is important since it affects: (1) the comfort level associated with wearing the pad; (2) the amount of panty area covered by the pad (i.e., is relevant to the prevention of panty soiling experiences); and (3) the visual appearance of the pad after use. These compressive forces are often measured as the amount of force necessary to hold the central portion of the catamenial pad compressed in the cross (width) direction in both the dry and wet states. The resiliency of the pad is often measured as both the % recovery relative to the initial width of the pad and the absolute width recovered in the central portion of the pad after it has been subjected to cross directional compression. The % recovery of the pad after wet lateral compression has been found to correlate to the visual appearance of the product after use.

Similarly, since catamenial users make visual assessments of the pad after it has been worn for a period of time (i.e., when checking or removing the pad), and the wet state of the pad is more critical to sustained area coverage of the panty than is the dry state, the pad is more than likely to contain some amount of fluid. Thus, the wet state is important to the visual appearance of the product after use. Pads which recover (at the center) from the wet compressed state at least about 65% (preferably at least about 75%) of their initial width appeal to catamenial users for their visual appearance after use. Pads according to the present invention typically recover after wet compression from about 55 to about 90% (more typically from about 75 to about 85%) of the initial pad width.

The following table presents the mechanical properties of a representative absorbent article constructed according to the embodiment depicted in FIG. 2, utilizing the preferred materials as outlined below.

TABLE 2

| | Force (g) | Initial Width (cycle 1) (mm) | Initial Width (cycle 6) (mm) | Wet Recovery (%) |
|---|---|---|---|---|
| Dry condition | 171 | 64.45 | 57.23 | 88.8 |
| Wet condition | 113 | 64.97 | 53.60 | 82.5 |

See the Test Methods section for the procedure to measure the compressive force values in the dry state, and the absolute and relative recovery from compression (i.e., resiliency) in the wet state of catamenial pads and related catamenial products.

E. Test Methods

1. Compressive Force and Recovery Test

In this test, the center of a catamenial pad is subjected to 6 cycles of compression across its width, followed by release of the compressive forces. (This test can also be used with other catamenial products such pantiliners). The pad is compressed by a pair of plates designed to simulate forces and constraints experienced during wear. The distance traveled by the plates and the resulting forces are measured.

2. Apparatus and Sample Preparation

Figure 5:
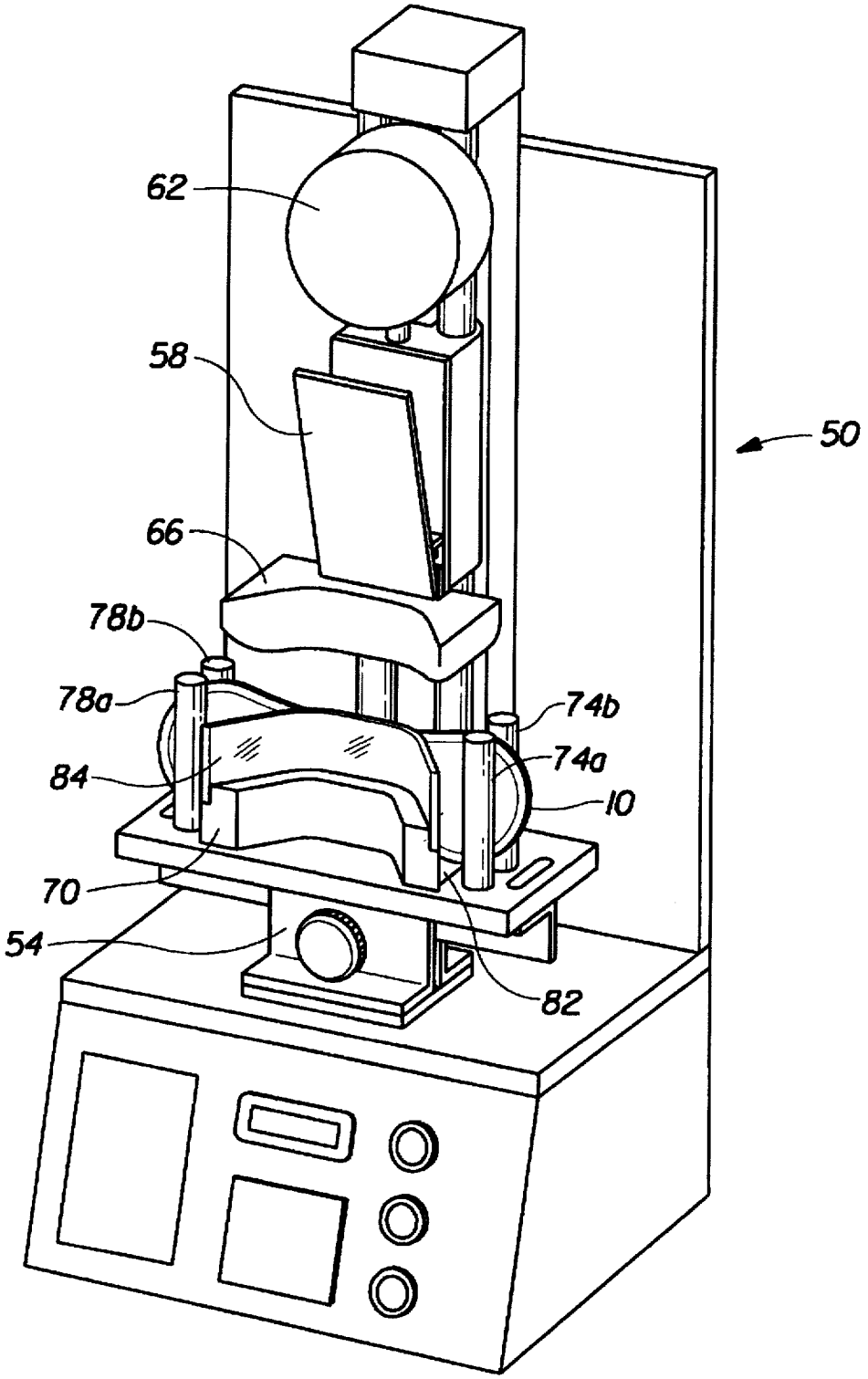
FIG. 5 is a perspective view of an instrument for measuring the compressive force and resiliency of a catamenial pad.

Suitable equipment for carrying out this test include, for example, Instron Model 1122 and EME Model 599A instruments. FIG. 5 shows this test being performed with an EME 599A instrument indicated generally as 50. Instrument 50 includes an fixed lower clamp 54 and an upper reciprocating clamp 58. Instrument 50 also includes a weight (4000 g) indicated generally as 62 for biasing upper clamp 58 downwardly.

Compressive forces are applied to the pad 10 by an assembly 64 (see FIGS. 6 and 7) comprised of a pair of plates 66 and 70. The upper compression plate 66 simulates one thigh of the wearer. The lower compression plate 70 simulates both the opposite thigh of the wearer and the portion of the body (the perineal area) contacting the pad 10 during use. The lower compression plate 70 also contains two pairs of spaced cylindricals posts 74*a*, 74*b*, 78*a*, and 78*b*, one pair on each side of main body portion 82 of lower plate 70, as well as a Plexiglass viewing screen 84 mounted on top of body portion 82. These posts hold the pad 10 in position during the course of testing.

Figure 6:
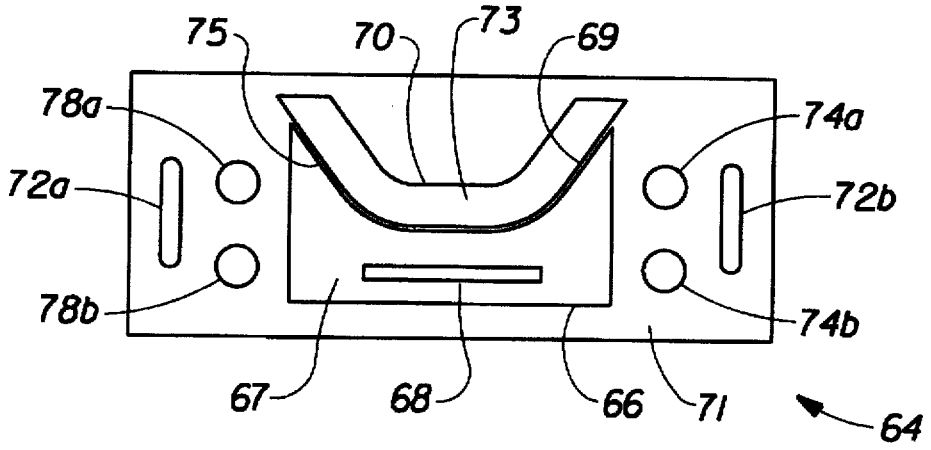
FIG. 6 is a top plan view of the compression plate assembly used in measuring the compressive force and resiliency of the catamenial pad.
Figure 7:
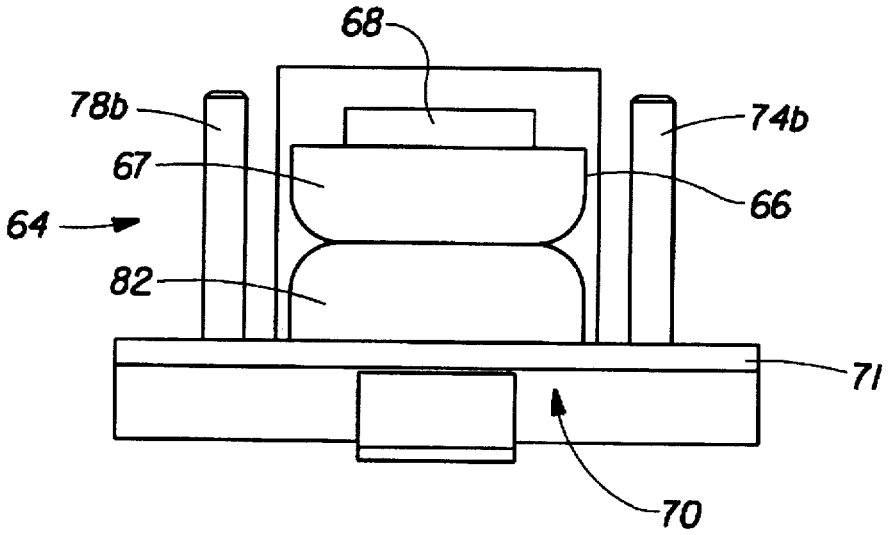
FIG. 7 is a side view of the compression plate assembly shown in FIG. 6.

Referring to FIGS. 6 and 7, lower plate 70 comprises a base 71 in which are formed a pair of spaced lots 72*a* and 72*b* that are used to secure plate 70 to lower clamp 54 of instrument 50. As particularly shown in FIG. 6, main body portion 82 of plate 70 has an upper part 73 provided with a convex, curved face 75.

Figure 8:
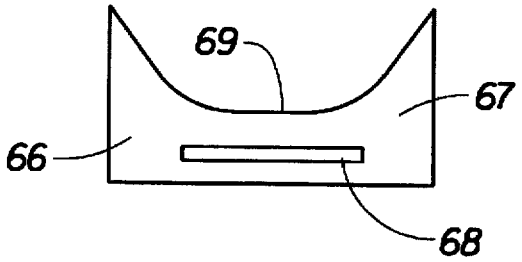
FIG. 8 is a top plan view of the of the upper compression plate of the compression plate assembly shown in FIGS. 6–7.
Figure 9:
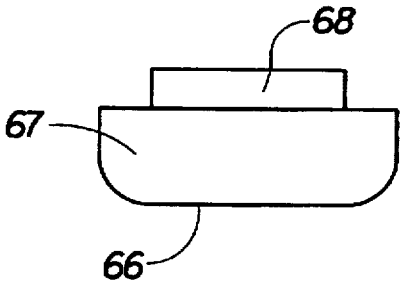
FIG. 9 is a side view of the upper compression plate assembly shown in FIG. 8.

As particularly shown in FIGS. 8 and 9, upper plate 66 has a main body portion 66 that is provided with a concave, curved face 69. Attached to body portion 67 is a generally rectangular mounting bracket 68 for securing the upper plate 66 to the reciprocating upper clamp 58 of instrument 50. As particularly shown in FIG. 6, convex face 75 of lower plate 70 is opposed and configured so as to fit within concave face 69 of upper plate 66. This configuration allows upper plate 66 to move past lower plate 70 in close proximity thereto, but without faces 75 and 69 coming into contact. As shown particularly in FIG. 6, when upper plate 66 moves completely down, it fits together with lower plate 70 but without coming into physical contact.

The plates 66 and 70 (and their constituent parts) can be made from any suitable material (e.g., aluminum, Lexan, Plexiglass) that can be formed into the required shape. However, the weight of assembly 64 comprising plates 66 and 70 must be significantly lower than the limit of the instrument load cell to allow sufficient range for the force measurement.

During the test, the crosshead speed (i.e., the rate at which upper plate 66 moves downward during the compression cycle) is 22 inches/minute. The gap between the upper part 73 of main body portion 82 of plate 70 and the bottom of main body portion 67 of plate 66 starts at a distance of 4 inches, and then narrows to a 1 inch gap distance when pad 10 is fully compressed.

Samples of catamenial pad 10 are equilibrated for a minimum of two hours at 73±2° F., and 50±2% relative humidity. Samples should be fully finished pads, including placement of adhesive and release paper on the bottom of the pad. Undue bending of the sample as it is being prepared should be avoided. A minimum of six samples of each pad 10 is required for the test.

a. Test Procedure

The release paper is removed from the pad 10 and the panty fastening adhesive is "deactivated" by lightly coating it with talc. Pad 10 is then placed between the pairs of posts 74*a*, 74*b*, 78*a*, and 78*b*, such that it is in the configuration of an arc with its ends pointing toward the main body portion 82 of plate 70, and should be loosely confined between the posts. Pad 10 is oriented such that it is standing up on one edge. The distance between the upper part 73 of main body portion 82 of plate 70 and the bottom of main body portion 67 of plate 66 should now be 4 inches.

The plate 66 is then moved towards plate 70 at a rate of 22 inches/minute by the downward motion of reciprocating upper clamp 58 until pad 10 has been compressed to 1 inch (full compression). Compression is maintained for 30 seconds. The distance at which the main body portion 67 of upper compression plate 66 makes contact with the edge of pad 10 is determined when a force of 10 g is reached. This is the initial width of the pad. The force at the end of the 30 seconds after full compression is reached, and immediately before the compression is released, is recorded as the compression force.

After 30 seconds of full compression, the compressive forces are released by moving plate 66 to its initial position (4 inches apart). Pad 10 is left uncompressed for 60 seconds. At the end of the 60 seconds, a second compression cycle is started. The same procedure as described before is carried out. This procedure is repeated until pad 10 has been subjected to 6 compression/release cycles.

Three dry samples of pad 10 are tested by this procedure. Three additional samples of pad 10 are then tested in the wet state by pouring 7.5 ml of 0.9% saline solution into the center of the samples (allowing the sample to distribute the fluid itself), followed by 10 minutes before testing begins. The wet samples are subjected to the same procedure as the dry samples.

b. Calculations

After 3 dry samples and wet samples are run, the following values are determined:

(1) The average compression force from cycle 6 on the three dry pads;

(2) The average initial pad width from cycle 1 on the three wet pads;

(3) The average initial pad width from cycle 6 on the three wet pads;

(4) The average percent wet recovery on the three wet pads is calculated using the following equation:

% wet recovery=100×(initial pad width for cycle 6+initial pad width for cycle 1)

F. Preparation of Catamenial Pads Having Improved Resistance to Bunching

Catamenial pads are constructed as follows. All materials are precut into the desired shapes (see FIG. 1). The absorbent structure layers are cut into the desired finished shapes. The topsheet and backsheet are cut into rectangles measuring 127 mm by 292 mm.

Onto silicone-coated release paper a spiral pattern of H2031 Findlay hot melt adhesive is applied at 0.02 g. per $in^2$. This adhesive layer is transferred onto the bottom side of an apertured form film topsheet by rolling the topsheet and coated release paper together with a hand roller. The secondary topsheet is applied to the adhesive side of the topsheet and the two are bonded by rolling them together with a hand roller. Two strips of double sided-tape are applied on along both long sides of a polyethylene backsheet. The other layers of the absorbent core are added one at a time to construct the complete absorbent structure.

To construct a representative absorbent article according to the embodiment of FIG. 2, the following materials are utilized for the components of the absorbent structure. The secondary topsheet 14 is formed of a nonwoven material known as P-9 commercially available from Fiberweb North America. Fluid distribution layer 24 is formed of standard airfelt (unbonded cellulosic material). The fluid storage layer 26 is formed of an AGM-containing web formed of thermally-bonded fibrous material. The resilient web 28 is constructed of 100% synthetic, 100% bicomponent thermoplastic polyethylene/polypropylene fibers as detailed above. The secondary topsheet is adhesively bonded to the topsheet and the distribution layer by hot melt adhesive. The storage layer is adhesively bonded to the distribution layer and the resilient web by hot melt adhesive.

The topsheet and absorbent structure assembly are then combined. Next, a sheet of Teflon® is placed over the assembled structure. The edges of the product are sealed with an appropriately shaped die, attached to an iron and heated to a temperature above the melting point of the polyethylene topsheet and backsheet. The iron die is applied to the material with hand pressure to seal the edges. The catamenial pad is then cut from the excess material using a pair of hand scissors.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A catamenial pad capable of acquiring, distributing and storing aqueous body fluids, which comprises:

(a) a fluid pervious topsheet;

(b) a fluid acquisition layer adjacent said topsheet;

(c) an absorbent core in fluid communication with at least one of said topsheet and said fluid acquisition layer;

(d) an omnidirectionally resilient web in fluid communication with said absorbent core, said resilient web comprising between about 50% and about 100% individual fibers of a synthetic material bonded together into a thermally-bonded, fluid-pervious matrix, said resilient web having a wet density of less than about 0.07 g/cc at 0.29 psi; and (e) a fluid impervious backsheet;

wherein said resilient web exhibits sufficient omnidirectional resiliency to provide said catamenial pad with a wet recovery of at least about 65%.

2. The catamenial pad of claim 1, wherein said resilient web exhibits sufficient omnidirectional resiliency to provide said catamenial pad with a wet recovery of at least about 75%.

3. The catamenial pad of claim 1, wherein said resilient web is located between said topsheet and said absorbent core.

4. The catamenial pad of claim 1, wherein said resilient web is located between said absorbent core and said backsheet.

5. The catamenial pad of claim 1, wherein said absorbent core comprises at least two layers, and wherein said resilient web is located between said layers of said absorbent core.

6. The catamenial pad of claim 1, wherein said resilient web is adjacent to a layer within said absorbent core which contains particles of absorbent gelling material, such that said resilient web permits expansion of said particles of absorbent gelling material.

7. The catamenial pad of claim 1, wherein said resilient web comprises about 100% synthetic material.

8. The catamenial pad of claim 7, wherein said synthetic material comprises a thermoplastic bicomponent material.

* * * * *